(12) United States Patent
Richard

(10) Patent No.: US 11,696,801 B2
(45) Date of Patent: Jul. 11, 2023

(54) METHOD AND SYSTEM FOR VALIDATING BONE ALTERATIONS IN COMPUTER-ASSISTED SURGERY

(71) Applicant: ORTHOSOFT ULC, Montreal (CA)

(72) Inventor: Alain Richard, Lachine (CA)

(73) Assignee: ORTHOSOFT ULC, Montreal (CA)

( * ) Notice: Subject to any disclaimer, the term of this patent is extended or adjusted under 35 U.S.C. 154(b) by 433 days.

(21) Appl. No.: 17/078,191

(22) Filed: Oct. 23, 2020

(65) Prior Publication Data

US 2021/0121234 A1 Apr. 29, 2021

Related U.S. Application Data

(60) Provisional application No. 62/924,925, filed on Oct. 23, 2019.

(51) Int. Cl.
*A61B 34/10* (2016.01)
*A61B 34/20* (2016.01)

(52) U.S. Cl.
CPC .............. *A61B 34/10* (2016.02); *A61B 34/20* (2016.02); *A61B 2034/104* (2016.02); *A61B 2034/105* (2016.02); *A61B 2034/107* (2016.02); *A61B 2034/2055* (2016.02)

(58) Field of Classification Search
CPC combination set(s) only.
See application file for complete search history.

(56) References Cited

U.S. PATENT DOCUMENTS

2012/0323244 A1* 12/2012 Cheal ................. A61B 34/10
606/130

* cited by examiner

*Primary Examiner* — Sameh R Boles
(74) *Attorney, Agent, or Firm* — Horton Rose Fulbright Canada LLP

(57) ABSTRACT

A system for validating bone alterations during computer-assisted surgery, comprises a processing unit; and a non-transitory computer-readable memory communicatively coupled to the processing unit and comprising computer-readable program instructions executable by the processing unit for: registering a surface of a bone in a coordinate system using a geometry of a patient specific tracker device on the surface of the bone; tracking a tool relative to the bone in the coordinate system as a function of implant geometry and of a planned implant position and orientation on the bone; and validating at least one alteration to the bone using a mating geometry of a validation tracker device applied to an altered surface of the bone.

20 Claims, 8 Drawing Sheets

METHOD AND SYSTEM FOR VALIDATING BONE ALTERATIONS IN COMPUTER-ASSISTED SURGERY

CROSS-REFERENCE TO RELATED APPLICATION

The present application claims the priority of U.S. Patent Application Ser. No. 62/924,925, filed on Oct. 23, 2019, the contents of which are incorporated herein by reference.

TECHNICAL FIELD

The present application relates to orthopedic computer-assisted surgery and to patient-specific instrument and optical tracking, for instance in the field of robotic surgery.

BACKGROUND OF THE ART

Computer-assisted surgery commonly employs tracker devices that are secured to bones and/or to surgical tools, for the subsequent tracking of tools relative to bones. In order to ensure that the tracking is accurate, the tracker devices may be connected to bones in an invasive manner. For instance, tracker devices may be pinned to bones, creating holes in thinner bone portions such as in parts of a scapula, in a bone shaft, etc. The act of pinning the tracker devices can lead to fractures in the bone, such as the femur or tibia in computer-assisted knee replacement surgery. Some technologies, such as patient-specific instrumentation, may assist in rendering bone tracking less invasive.

SUMMARY

In accordance with one aspect of the present disclosure, there is provided a system for validating bone alterations during computer-assisted surgery, comprising: a processing unit; and a non-transitory computer-readable memory communicatively coupled to the processing unit and comprising computer-readable program instructions executable by the processing unit for: registering a surface of a bone in a coordinate system using a geometry of a patient specific tracker device on the surface of the bone; tracking a tool relative to the bone in the coordinate system as a function of implant geometry and of a planned implant position and orientation on the bone; and validating at least one alteration to the bone using a mating geometry of a validation tracker device applied to an altered surface of the bone.

In accordance with another aspect of the present disclosure, there is provided a system for validating bone alterations during computer-assisted surgery, comprising: a tracking apparatus; a patient-specific tracker device with a trackable reference, the patient specific tracker device having at least one contact surface being a negative of a pre-operative surface of the bone; a validation tracker device with a trackable reference, the patient specific tracker device having at least one contact surface for mating with an alteration on the bone; a processing unit; and a non-transitory computer-readable memory communicatively coupled to the processing unit and comprising computer-readable program instructions executable by the processing unit for: registering the pre-operative surface of the bone in a coordinate system using a geometry of the patient-specific tracker device and readings from the tracking apparatus; tracking a tool relative to the bone in the coordinate system as a function of implant geometry and of a planned implant position and orientation on the bone, using readings from the tracking apparatus; and validating at least one alteration to the bone using a mating geometry of the validation tracker device applied to an altered surface of the bone.

DETAILED DESCRIPTION

Figure 1:
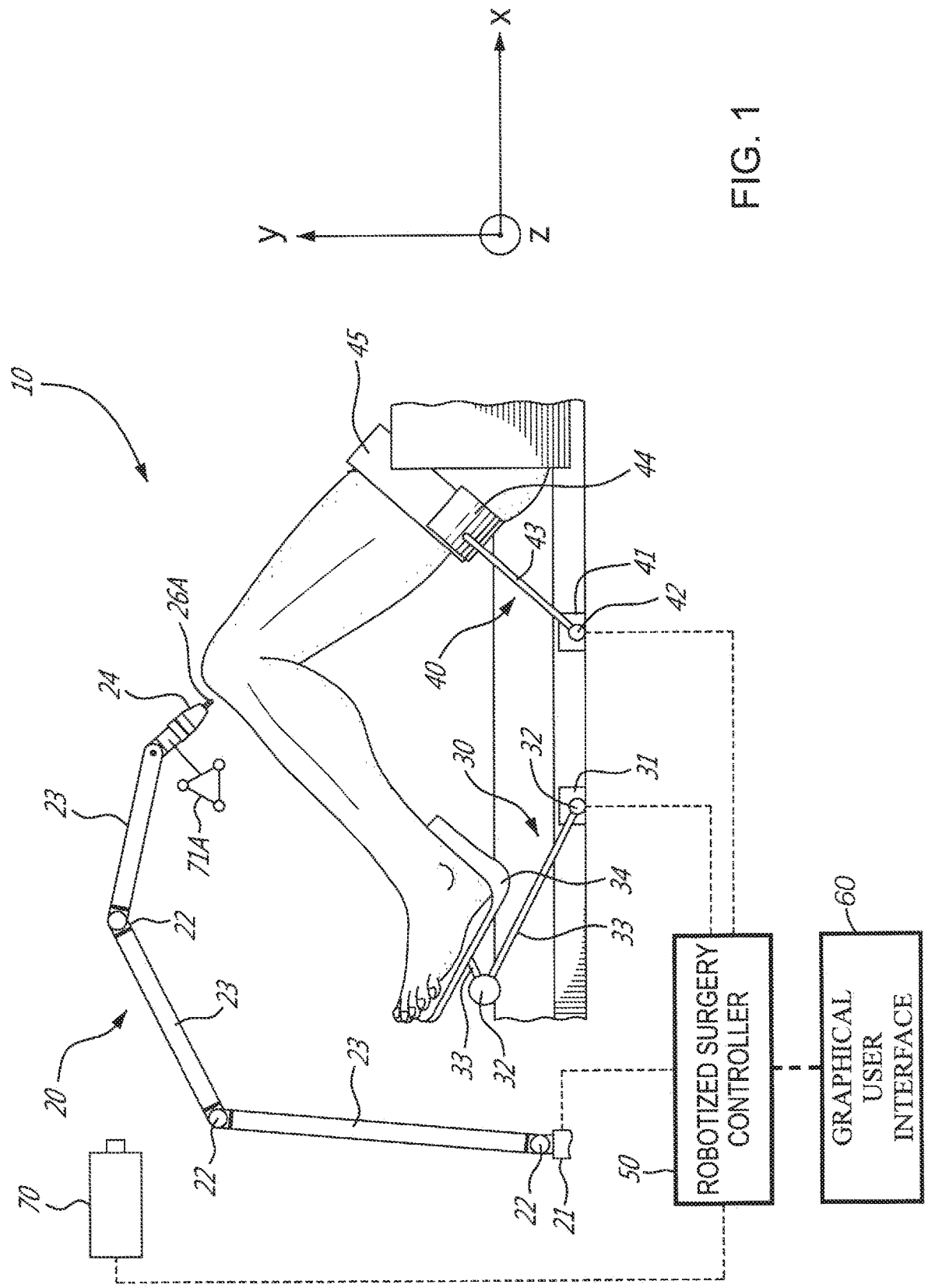
FIG. 1 is a schematic view of a CAS system for validating bone alterations in accordance with the present disclosure.

Referring to FIG. 1, a computer-assisted surgery (CAS) system in accordance with the present disclosure is generally shown at 10. The CAS system 10 may be used to perform at least some of the steps of method 100 of FIG. 2. The CAS system 10 is shown relative to a patient's knee joint in supine decubitus, but only as an example. The system 10 could be used for other body parts, including non-exhaustively hip joint, spine, and shoulder bones.

The CAS system 10 may or may not be robotized, hence the CAS system 10 may have some of the following components, depending on the contemplated use with or without robotizing: a robot arm 20, a foot support 30, a thigh support 40, a CAS controller 50, a GUI 60, and a tracking apparatus 70:

The robot arm 20 is the working end of the CAS system 10 when used in a robot configuration, and is used to perform bone alterations as planned by an operator and/or the CAS controller 50 and as controlled by the CAS controller 50;

The foot support 30 supports the foot and lower leg of the patient, in such a way that it is only selectively movable. The foot support 30 is robotized in that its movements can be controlled by the CAS controller 50. The foot support 30 may or may not be present in the robotic configuration;

The thigh support 40 supports the thigh and upper leg of the patient, again in such a way that it is only selectively or optionally movable. The thigh support 40 may optionally be robotized in that its movements can be controlled by the CAS controller 50. The thigh support 40 may or may not be present in the robotic configuration; In shoulder replacement surgery, an analogous arm support may be used.

The CAS controller 50 operates the surgical workflow and at least part of the method 100. The CAS controller 50 may also control the robot arm 20, the foot support 30, and/or the thigh support 40, if the CAS system 10 has a robotic configuration. The CAS controller 50 may therefore include a non-transitory computer-readable memory communicatively coupled to the one or more processing units and may comprise computer-readable program instructions executable by one or more processing units to operate tasks and a surgical workflow such as that of the method 100 described herein. The CAS controller 50 may also guide an operator through the surgical procedure, by providing intraoperative data of position and orientation, and may therefore have the appropriate interfaces such as mouse, footpedal etc;

A GUI 60 provides visual guidance through the workflow of the CAS system 10, and/or during the method 100. The GUI 60 may be part of a monitor, touchscreen, tablet, etc; and The tracking apparatus 70 may be used to track the bones of the patient and/or tools, and the robot arm 20 if present. For example, the tracking apparatus 70 may assist in performing the calibration of the patient bone with respect to the robot arm 20, or registration of the patient bone, for subsequent navigation in the X, Y, Z coordinate system.

The CAS system 10 may be without the robot arm 20, with the operator performing manual tasks. In such a scenario, the CAS system 10 may only have the CAS controller 50, GUI 60 and the tracking apparatus 70. The CAS system 10 may thus be used without robotic assistance, and assists operator by way of surgical navigation. The CAS system 10 may also have non-actuated foot support 30 and thigh support 40 to secure the limb. When it operates the robot arm 20, the CAS system 10 may drive the robot arm 20 autonomously, and/or as an assistive or collaborative tool for an operator (e.g., surgeon).

Still referring to FIG. 1, a schematic example of the robot arm 20 is provided. The robot arm 20 may stand from a base 21, for instance in a fixed relation relative to the operating-room (OR) table supporting the patient. The relative positioning of the robot arm 20 relative to the patient is a determinative factor in the precision of the surgical procedure, whereby the foot support 30 and thigh support 40 may assist in keeping the operated limb fixed in the illustrated X, Y, Z coordinate system, used by the method 100. The robot arm 20 has a plurality of joints 22 and links 23, of any appropriate form, to support a tool head 24 that interfaces with the patient. The tool head 24 may be a registration pointer, rod or wand, ranging laser, radiation/light transmitter, laser telemeter, to register the bone(s). Registration may also be known as digitizing, and may be defined as recording coordinates of a point or surface in a referential coordinate system, also known as a frame of reference. In FIG. 1, the X,Y,Z coordinate system is shown, and is a virtual coordinate system, and registration may be recording x,y,z coordinates of points in the X,Y,Z coordinate system, as an example. Depending on the type of procedure, the registration may entail a robotic or manual manipulation of a registration pointer contacting points on the surface of the bone, including cartilage, for the points to be registered (i.e., recorded, digitized). Registration may also be done by ranging, for example using a laser with ranging capability (e.g., measuring a distance). Stated differently, registration described herein may be contactless, namely in the form of a radiation transmitter, for example a light transmitter, such as a laser beam, coupled to a distance sensor. In particular, said identification means can be in the form of a laser telemeter. In an embodiment, the laser is manipulated by a robotic arm, such as the robot arm 20. Alternatively, an ultrasound transducer may be used instead of or with a laser telemeter or other contactless registration device.

The arm 20 is shown being a serial mechanism, arranged for the tool head 24 to be displaceable in a desired number of degrees of freedom (DOF). For example, the robot arm 20 controls 6-DOF movements of the tool head 24, i.e., X, Y, Z in the coordinate system, and pitch, roll and yaw. Fewer or additional DOFs may be present. For simplicity, only a generic illustration of the joints 22 and links 23 is provided, but more joints of different types may be present to move the tool head 24 to desired position and orientation in the manner described above. The joints 22 are powered for the robot arm 20 to move as controlled by the controller 50 in the six DOFs. Therefore, the powering of the joints 22 is such that the tool head 24 of the robot arm 20 may execute precise movements, such as moving along a single direction in one translational DOF, or being restricted to moving along a plane, among possibilities. Such robot arms 20 are known, for instance as described in U.S. patent application Ser. No. 11/610,728, incorporated herein by reference.

In order to preserve the fixed relation between the leg and the coordinate system, and to perform controlled movements of the leg as described hereinafter, a generic embodiment is shown in FIG. 1. The foot support 30 may be displaceable relative to the OR table, in order to move the leg in flexion/extension (e.g., to a fully extended position and to a flexed knee position), with some controlled lateral movements being added to the flexion/extension. Accordingly, the foot support 30 is shown as having a robotized mechanism by which it is connected to the OR table, with sufficient DOFs to replicate the flexion/extension of the lower leg. Alternatively, the foot support 30 could be supported by a passive mechanism, with the robot arm 20 connecting to the foot support 30 to actuate its displacements in a controlled manner in the coordinate system. The mechanism of the foot support 30 may have a slider 31, moving along the OR table in the X-axis direction. Joints 32 and links 33 may also be part of the mechanism of the foot support 30, to support a foot interface 34 receiving the patient's foot. Moreover, while the leg is shown, the CAS system 10 could be used to perform orthopedic surgery on other body parts (e.g. shoulder).

Referring to FIG. 1, the thigh support 40 may be robotized, static or adjustable passively. In the latter case, the thigh support 40 may be displaceable relative to the OR table, in order to be better positioned as a function of the patient's location on the table. Accordingly, the thigh support 40 is shown as including a passive mechanism, with various lockable joints to lock the thigh support 40 in a desired position and orientation. The mechanism of the thigh support 40 may have a slider 41, moving along the OR table in the X-axis direction. Joints 42 and links 43 may also be part of the mechanism of the thigh support 40, to support a thigh bracket 44. A strap 45 can immobilize the thigh/femur in the thigh support 40. The thigh support 40 may not be necessary in some instances. However, in the embodiment in which the range of motion is analyzed, the fixation of the femur via the thigh support 40 may assist in isolating joint movements. Likewise, a support device may assist in securing the upper extremities in shoulder replacement surgery, either anatomical total shoulder arthroplasty or reverse shoulder arthroplasty.

Figure 2:
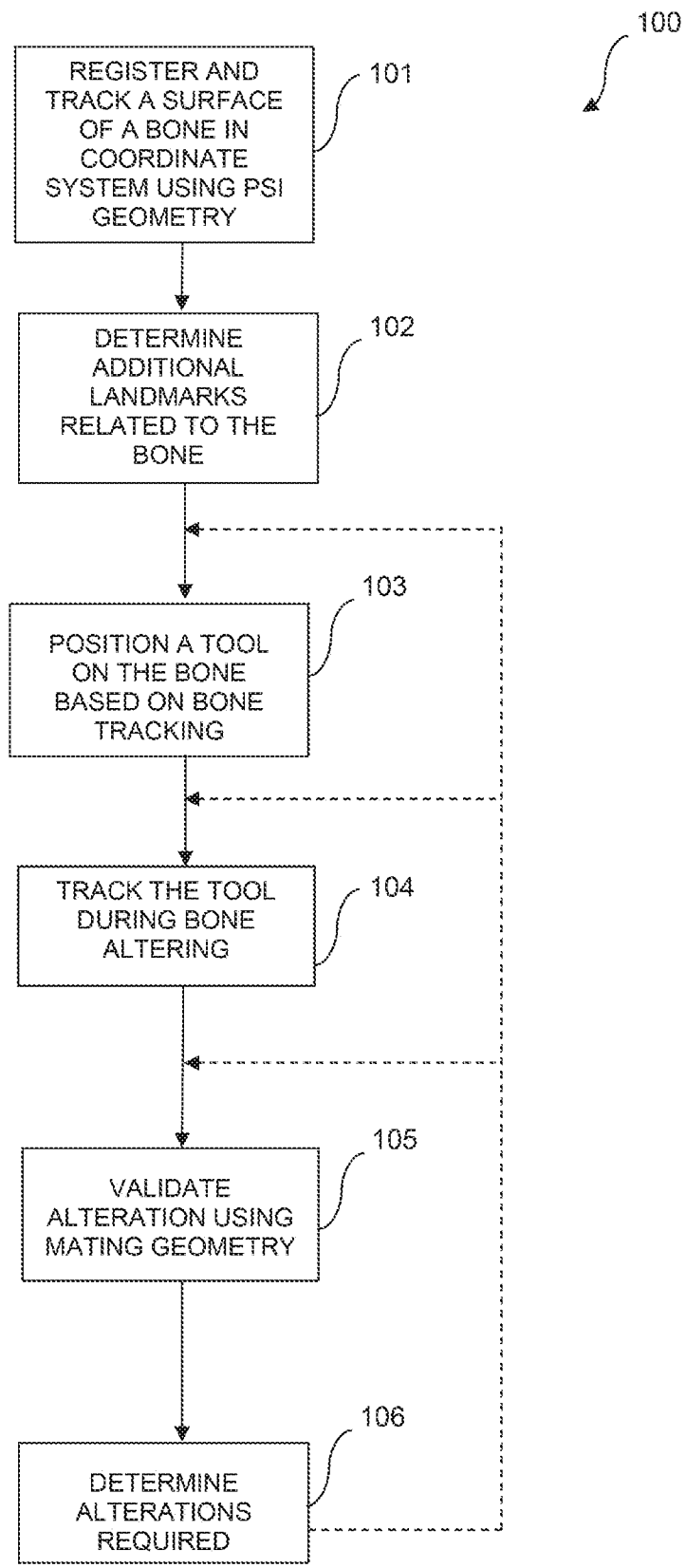
FIG. 2 is a flowchart depicting a CAS method for validating bone alterations in accordance with the present disclosure.

The CAS controller 50 has a processor unit to control movement of the robot arm 20, and of the leg support (foot support 30 and thigh support 40), if applicable. The CAS controller 50 provides computer-assisted surgery guidance to an operator, whether in the form of a navigation data, model assessment, etc in pre-operatively planning or during the surgical procedure. For instance, the navigation data may be in the form of a surgical workflow, by which the CAS controller 50 suggests a sequence of steps, including some steps related or present in method 100 (FIG. 2). The system 10 may comprise various types of interfaces, for the information to be provided to the operator, for instance via the GUI 60. The interfaces of the GUI 60 may be monitors and/or screens including wireless portable devices (e.g., phones, tablets), audio guidance, LED displays, among many other possibilities. If a robot arm 20 is present, the controller 50 may then drive the robot arm 20 in performing the surgical procedure based on the planning achieved pre-operatively. The controller 50 may do an intra-operative bone model assessment to update the bone model and fit it with accuracy to the actual bone, and hence enable corrective plan cuts to be made, or guide the selection of implants. The controller 50 may also generate a post-operative bone model. The CAS controller 50 runs various modules, in the form of algorithms, code, non-transient executable instructions, etc, in order to operate the system 10 in the manner described herein.

The use of the tracking apparatus 70 may provide tracking data to perform the bone model updating and subsequent surgical navigation. For example, the tracking apparatus 70 may assist in performing the calibration (i.e., digitizing, in the form of point registration) of the patient bone with respect to the coordinate system, for subsequent navigation in the X, Y, Z coordinate system. According to an embodiment, the tracking apparatus 70 comprises a camera that optically sees and recognizes retro-reflective references 71A, 71B (FIGS. 3 and 4), and 71C (FIG. 5)—concurrently, the references 71—so as to track the tools and limbs in six DOFs, namely in position and orientation. In an embodiment featuring the robot arm 20, the reference 71A is on the tool head 24 of the robot arm 20 such that its tracking allows the controller 50 to calculate the position and/or orientation of the tool head 24 and tool 26A thereon. The references 71 have spheres or patterns of retro-reflective material thereon, arranged in a known geometric arrangement (e.g., scalene triangle). The CAS controller 50 and/or the tracking apparatus 70 recognize the geometric arrangements, such that the position and orientation of the references 71 is trackable. Other tracking modalities may be used as an alternative to the retro-reflective material, include active tracking devices with transmitters and receivers, inertial sensors, etc.

References 71B and 71C may be fixed to the patient-specific devices, known as PSI. For clarity, reference to patient specific/PSI in the present application pertains to the creation of devices that have negative corresponding contour surfaces, i.e., a surface that is the negative opposite of a patient bone/cartilage surface, such that the patient specific surface conforms to the patient bone/cartilage surface, by complementary confirming unique engagement contact. PSI devices may be generated using fabrication techniques such as 3D printing (additive manufacturing), NC machining, laser sintering, fused deposition modelling, stereolithography, laminated object, electron beam melting product, a contour milling product, and computer numeric control product etc, as examples among others. The negative corresponding contour surfaces may be obtained via preoperative imaging (e.g., X-ray, MRI, etc).

In an embodiment without the robot arm 20, references such as reference 71A are on the navigated tools (including a registration tool) such that their tracking allows the controller 50 to calculate the position and/or orientation of the tools and register points on the bone. Likewise, references 71B and 71C may be interfaced to the patient bones, such as the femur prior to resection for reference 71B and the femur after resection for reference 71C. Therefore, the controller 50 may continuously update the position and/or orientation of the robot arm 20 and/or tools 26 and patient bones in the X, Y, Z coordinate system using the data from the tracking apparatus 70. As an alternative to optical tracking, the tracking system 70 may consist of inertial sensors (e.g., accelerometers, gyroscopes, etc) that produce tracking data to be used by the controller 50 to continuously update the position and/or orientation of the robot arm 20. Other types of tracking technology may also be used, including using the internal control system of the robot arm 20 (e.g., encoders) to determine the position and orientation of the tools 26, if the robot arm 20 is present.

Figure 3A:
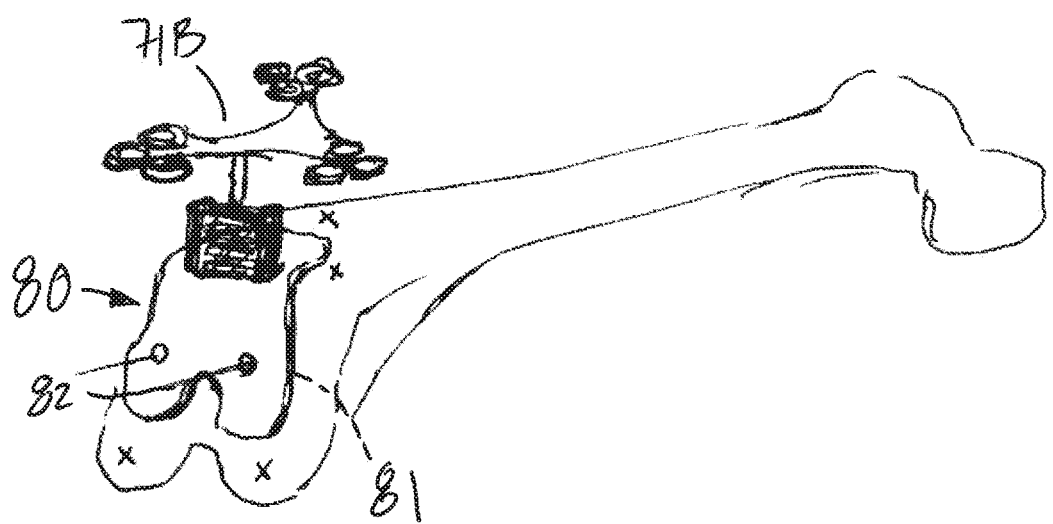
FIG. 3A is a schematic perspective view of a bone with a PSI tracker device used before resection of the bone.
Figure 3B:
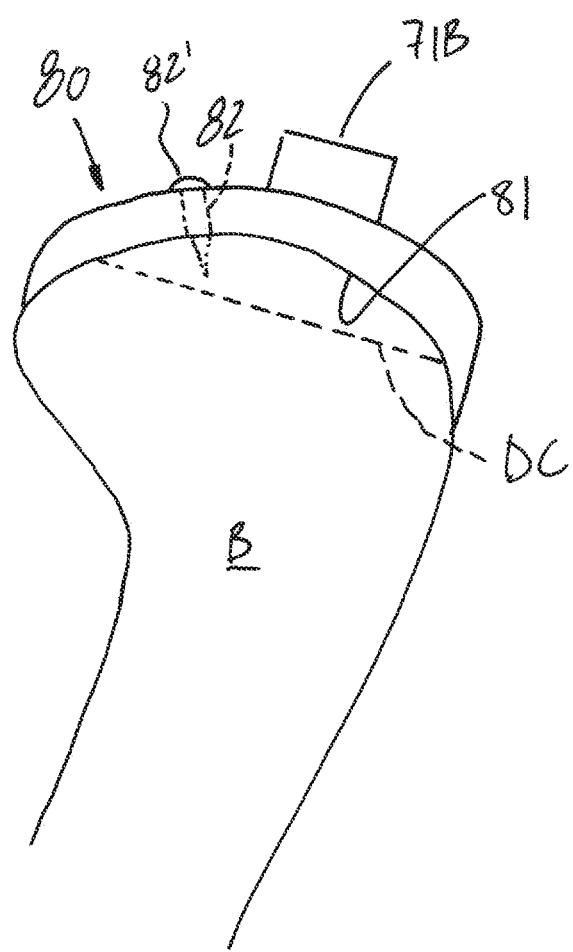
FIG. 3B is a schematic side view of the bone with the PSI tracker device of FIG. 3A.
Figure 4:
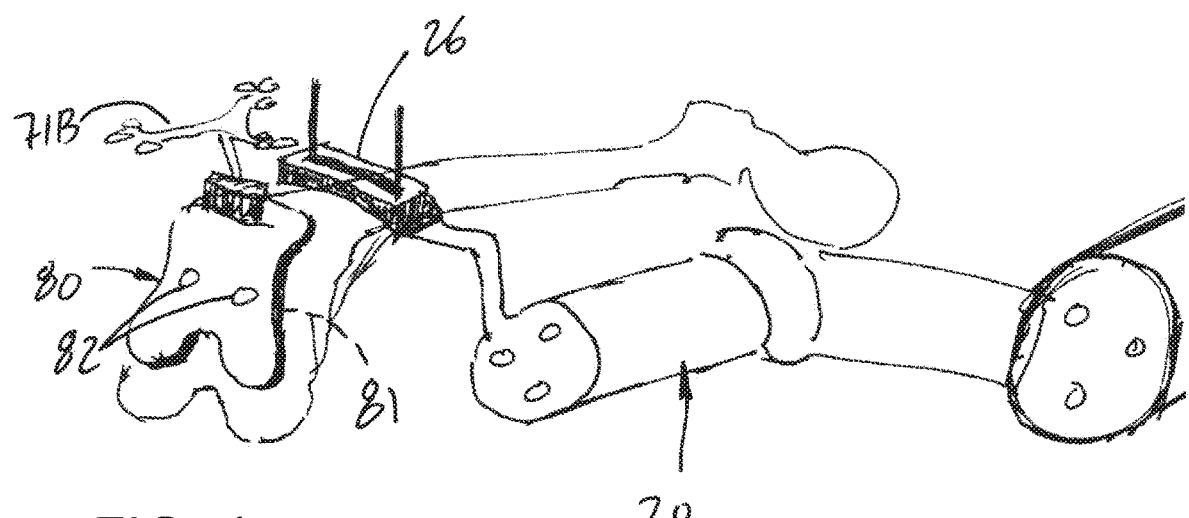
FIG. 4 is a schematic perspective view of the bone with the PSI tracker device of FIG. 3, with a cut guide.
Figure 6A:
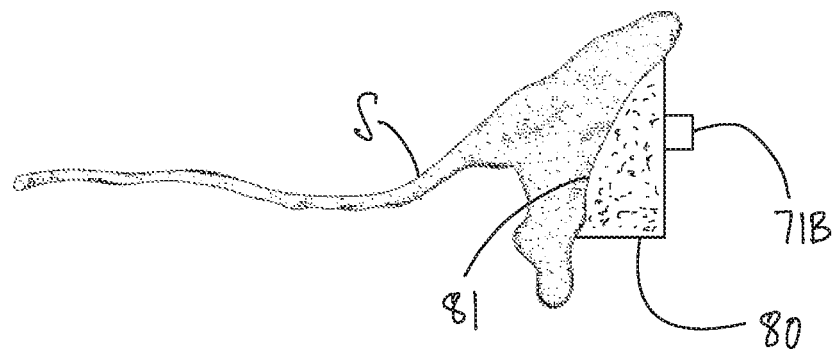
FIG. 6A is a schematic side view of a scapula with a PSI tracker device used before altering of the scapula.

In FIGS. 3A, 3B and 4, a PSI tracker device is generally shown at 80. The PSI tracker device 80 rigidly supports the reference 71B. The tracker device 80 has at least one PSI surface 81 that correspond to the preoperative surface of the bone that will be altered. In FIGS. 3A, 3B and 4, the PSI surface 81 forms a concavity that has at least one continuous surface of negative contact with the bone, though smaller spaced apart negative contact surfaces may be used additionally or alternatively, to enable unique complementary coupling of the PSI tracker device 80 to the bone, i.e., the conforming surfaces only enable a single possible position and orientation of the PSI tracker device 80 on the bone when the PSI surface 81 is against its negatively matching bone surface. For illustrative purposes, the PSI tracker device 80 is shown as being one that applies against the femur at the knee. However, the PSI tracker device 80 may be shaped to correspond to other bones, such as the tibia, the scapula (e.g., in the glenoid region, as in FIG. 6A), the humerus (FIG. 7A) etc. The PSI tracker device 80 may be said to be the pre-operative PSI tracker device 80, the pre-alteration or pre-resection PSI tracker device 80, the native PSI tracker device 80, etc, and is fabricated using a 3D model of a bone taken before bone resection. The PSI tracker device 80 may also be used in revision surgery. One or more attachment bores 82 may be provided in the body of the PSI surface 81, to attach the PSI tracker device 80 to the bone, if desired. The attachment bore(s) 82 may be optional, and may be for supporting a fastener 82', such as a screw. As also shown in FIG. 3A, bony landmark(s) "x" may be marked on the bone for subsequent check point verification. In an embodiment, the bony landmarks "x" are marked, and their portion relative to the PSI tracker device 80 is recorded in the coordinate system, for subsequent use. The bony landmark(s) "x" may be near predicted altered surfaces, but on native unaltered bone. The attachment bores 82 may also correspond to the planned pin locations for a subsequent instrument in the surgery. For example, the attachment bores may be designed to allow for the patient specific placement of a Persona 4-in-1 femoral cut guide (Zimmer Biomet, Warsaw, Ind.) to facilitate femoral anterior, posterior, and chamfer resections providing for placement of the femoral implant on the patient's femur at a planned femoral rotation.

Figure 5A:
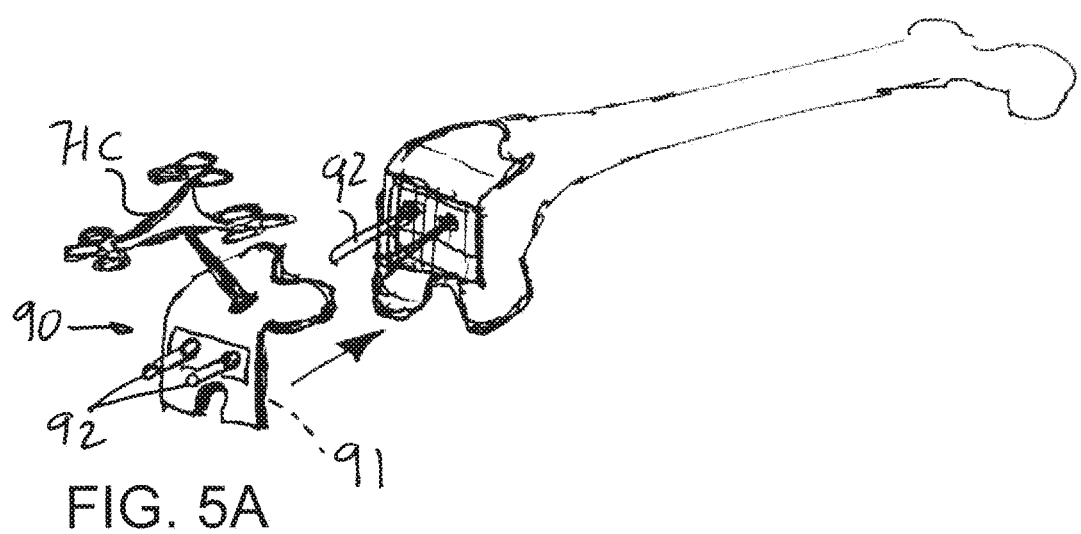
FIG. 5A is a schematic perspective exploded view of the bone of FIG. 3A with a validation tracker device, used after resection of the bone.
Figure 5B:
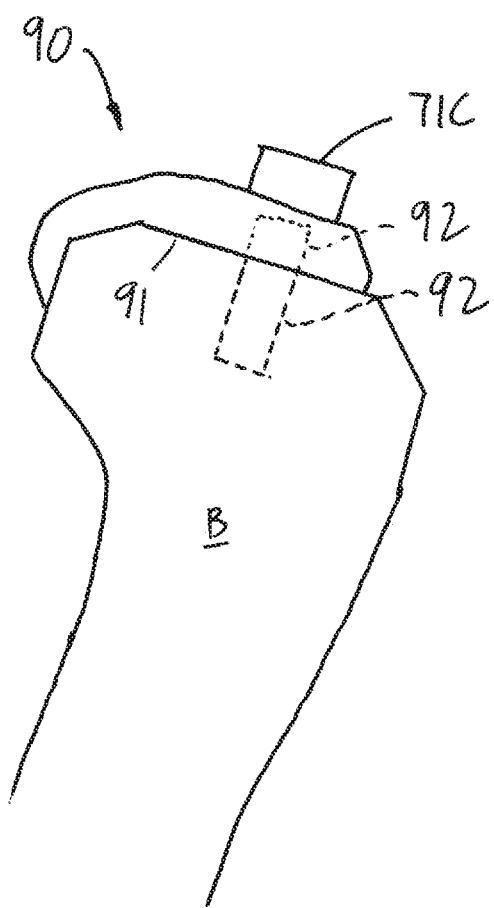
FIG. 5B is a schematic side view of the bone with the validation tracker device of FIG. 5A.
Figure 6B:
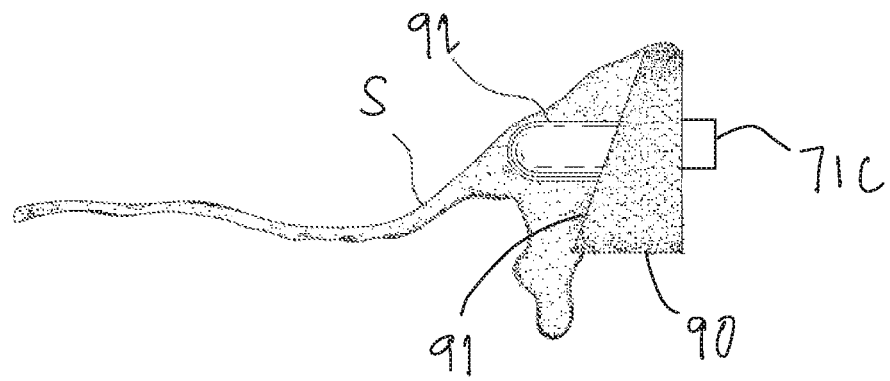
FIG. 6B is a schematic side view of the scapula of FIG. 6A with a validation tracker device, used after altering of the scapula.
Figures 7A, 7B:
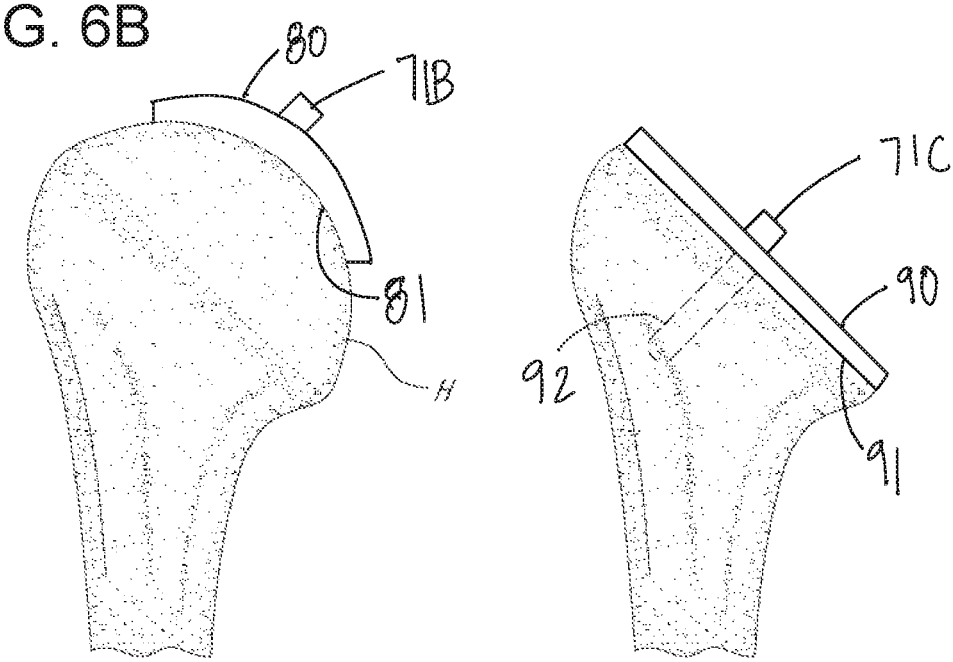
FIG. 7A is a schematic side view of a humerus with a PSI tracker device used before altering of the humerus.
FIG. 7B is a schematic side view of the humerus of FIG. 7A with a validation tracker device, used after altering of the humerus.

In FIGS. 5A and 5B, a validation tracker device is generally shown at 90. The validation tracker device 90 rigidly supports the reference 71C. The tracker device 90 has at least one bone contact surface 91 that may or may not have PSI surfaces. The contact surface(s) 91 aims to correspond to the altered surface of the bone. In an embodiment, the bone contact surface(s) 91 corresponds in part to native unresected (i.e., unaltered) bone surface and in part to the altered surface of the bone. For example, the contact surface(s) may be arranged to match the cut planes of the resected knee femur as in FIGS. 5A and 5B. As such, the geometry of the validation tracker device 90 may be based on the geometry of the selected implant, as the cut planes are also based on the geometry of the selected implant. The contact surface(s) 91 form a concavity that has at least one continuous surface of contact with the bone, though smaller spaced apart contact surfaces may be used additionally or alternatively. For illustrative purposes, the PSI tracker device 90 is shown as being one that applies against the resected femur at the knee, in complement to the PSI tracker device 80, e.g., as part of a same PSI kit. The validation tracker device 90 may be shaped to correspond to other bones, such as the tibia, the scapula (FIG. 6B), the humerus (FIG. 7B). The validation tracker device 80 may be said to be the intra-operative tracker device 90, the resection tracker device 90, the alteration tracker device 90, etc. In an embodiment, the validation tracker device 90 is fabricated using a 3D model of a planned resected bone. In another embodiment, the validation tracker device 90 is a stock device that is associated to a geometry of a selected implant. The implant selection dictates how the bone is to be resected. One or more verifications bore(s) or peg(s) 92 may be provided in the body of the validation tracker device 90, with the verification bores corresponding to the location of peg holes in the resected surface, which in turn correspond to the location of pegs in the implant. The verification bore(s) and the peg(s) 92 may be optional. Alternatively, the verification bores may also be used to drill planned pin locations for a subsequent instrument in the surgery. For example, the verification bores 92 may be designed to allow for the patient specific placement of a Persona 4-in-1 femoral cut guide (Zimmer Biomet, Warsaw, Ind.) to facilitate femoral anterior, posterior, and chamfer resections providing for placement of the femoral implant on the patient's femur at a planned femoral rotation subsequent to the distal femur resection. The validation tracker device may also include a separate set of bores (not shown in FIG. 5) for drill of the 4-in-1 guide pin holes distinct from the verification bores 91.

Referring now to FIG. 2, a method for tracking a bone in computer-assisted surgery is generally shown at 100. According to an embodiment, the method 100 is performed by the CAS system 10. Consequently, the method 100 may be embodied by computer-readable program instructions executable one or more processing units (e.g., of the CAS controller 50 or other component of the CAS system 10) as part of a non-transitory computer-readable memory communicatively coupled to the one or more processing units of the CAS controller 50. The method 100 is described with reference to the resection of a femur at the knee, to define cut planes upon which a selected implant will lie. However, in spite of the reference to the resection of a femur, the method 100 may be applied to other surgical procedures and/or to alter other bones, including the tibia with a resection of the tibial plateaus, the scapula for reverse glenoid surgery, the humerus for anatomical shoulder arthroplasty, etc.

According to 101, a position and/or orientation of a surface of a bone is registered and may then be tracked in a coordinate system using a PSI geometry. With reference to FIG. 3A, the position and/or orientation of the bone may be performed with the PSI tracker device 80 placed against the bone in the unique complementary engagement resulting from the use of the PSI surface 81. The geometry of the PSI tracker device 80, including the spatial relation between the PSI surface 81 and the reference 71B, may be known to the CAS system 10, for instance by using a virtual model of the PSI tracker device 80 including the PSI surface 81 in relation to the reference 71B. Therefore, if the PSI tracker device 80 is against the bone in the unique complementary engagement resulting from the use of the PSI surface 81, the bone surface against which the PSI tracker device 80 may be registered in the X,Y,Z coordinate system (or equivalent). If the PSI tracker device 80 remains on the bone, the bone surface may be continuously tracked in position and orientation relative to the X,Y,Z coordinate system. For this purpose, the PSI tracker device 80 may be tied to the bone using one or more fasteners received in the attachment bore(s) 82. As the robustness of the connection between the PSI tracker device 80 and the bone is caused by the complementary contact surfaces, the depth of fasteners may be limited, and may be less than a depth of resection—the fasteners would not be locating features, but would merely be to ensure the PSI surface 81 remains in the unique complementary contact with the bone.

Consequently, 101 includes the registration using the geometry of the PSI tracker device 80. If the bone is fixed in the X,Y,Z coordinate system, the position and orientation of the bone surface may be constant, and thus no tracking, or no active tracking may be required. The fixing of the bone may for instance be by which of the foot support 30 or tight support 40. An arm brace could be use to hold the humerus fixed if desired, in a reverse glenoid surgery.

According to 102, additional landmarks related to the bone may be determined. Stated differently, other landmarks may be registered for subsequent tracking. In an embodiment, with the PSI tracker device 80 secured to the bone in the manner shown in FIGS. 3A and 3B, kinematics may be performed to determine such landmarks. For example, rotational movements of the femur may be done to calculate the location of the center of the femoral head. In an embodiment, the pelvis is fixed in the X,Y,Z coordinate system. Alternatively, a reference 71 is fixed on the pelvis during the kinematics. With the center of the femoral head, a mechanical axis may be registered (i.e., digitized, recorded) in the coordinate system, with the geometry of the PSI tracker device 80 having another point of the mechanical axis.

In another embodiment, the determination of additional landmarks related to the bone may include using a registration pointer or equivalent (laser telemeter, etc) to obtain additional reference points on the bone. This may include driving the robot arm 20 to obtain such points. In the case of the femur, the other landmark points may include non-altered surfaces of the bone, such as the lateral epicondyle and the medial epicondyle. In an embodiment, the tracking of the reference 71B occurs throughout 102. In another embodiment, if the bone is fixed, the tracker device 80 may be removed, for example before 102 or at a later point.

According to 103, a tool is positioned on the bone based on the bone tracking and/or position and orientation of the bone surface, in the coordinate system. As shown in FIG. 4, the tool 26 may be a cut guide that is handled by the robot arm 20. The robot arm 20 may use its effector end to position and orient the cut guide 26 as a function of the position and orientation of the bone surface. In an embodiment, the tracking of the references 71A (FIG. 1) and 71B occurs throughout 103. In another embodiment, if the bone is fixed, the tracker device 80 may be removed before 103. The cut guide 26 may be drilled or pinned once it is in the desired position and orientation relative to the bone. If the cut guide 26 is attached to the robot arm, as depicted in FIG. 4, the bone may be tracked in the X, Y, Z coordinate system through position encoders on the joints of the robot arm, without reference to the tracker device 80.

The position and/or orientation of the tool 26 relative to the bone may be calculated by the CAS system 10 in 103 as a function of the 3D model of the bone and of the geometry of the implant, for instance based on a planned implant position and orientation. The planned position and orientation may be from a pre-operative planning, or may be intra-operative, such as by the placement of the implant model on a bone image in overlaid fashion. The 3D geometry of the implant may be accessible by the CAS system 10, for instance in the form of a digital 3D model featuring the implant contact planes, pegs, etc. The implant may be selected in preoperative planning, or even peri-operatively or intraoperatively. The location of bone alterations (e.g., location of drilling holes, cut planes, etc) is directly affected by implant geometry.

According to 104, the tool 26 is tracked during bone altering. In an embodiment, 104 is optional, in that the positioning of the tool may result in the securing of the tool to the bone. For example, if, as a result of 103, the cut guide 26 is secured to the bone, it may not be necessary to track a cut blade, or track the robot arm 20 during resection of the bone. As an example of tool tracking in 104, in the case of the femur alterations as visually exemplified in FIG. 4, the robot arm 20 may be tracked while drilling peg holes. The peg holes correspond to the location of pegs in the implant. Moreover, 104 may include redundant tracking, to ensure that a cut blade is in the desired orientation relative to the bone, in spite of the positioning having occurred in 103.

According to 105, alterations are validated. In an embodiment, the alterations may be validated using a mating geometry between the resected bone and the validation tracker device 90. The validation tracker device 90 is positioned against the resected surfaces of the bone as in FIGS. 5A, 5B—this may include unaltered surfaces as explained above. For this purpose, pegs or pins may be placed in the peg holes (e.g., resulting from alterations made during 104) to assist in locating the validation tracker device 90 in complementary contact with the bone. The complementary contact would occur due to the alterations (and unaltered if applicable) and the geometry of the validation tracker device 90 both being as a function of implant geometry. The operator may have a preliminary review of fit by mechanical interference when placing the validation tracker device 90 against the bone with the cooperation between the pegs 92 in the peg holes and/or the verification bores. The CAS system 10 in 105 may calculate the position and orientation of the alterations (e.g., planes in the illustrated embodiment) using the 3D geometry of the validation tracker device 90, in the coordinate system. Stated differently, the CAS system 10 in 105 may locate one or more of the alterations relative to the bone, The validation of 105 may consequently include the quantification of a variation off of the planned or expected position and/or orientation of the alterations. In the embodiment of FIGS. 3A to 5B, the quantification of variation may be in the form of varus or valgus angle, of depth of a cut, etc. The validation of 105 may also include a confirmation that the alterations are within acceptable range, and are thus as planned or expected. In such a scenario, a surgical workflow may be concluded after 105.

The validation of 105 may also include the tracking of the bone to identify the position and/or orientation of the alterations. For example, in the embodiment of FIGS. 5A and 5B, the kinematics performed in the 102 could be repeated to locate landmarks, such as the center of the femoral head. Likewise, the validation of 105 may include registering once more the landmarks (e.g., lateral epicondyle and medial epicondyle, bony landmark(s) "x" of FIG. 3A) relative to the validation tracker device 90 to determine the accuracy of the alterations. These landmarks may be the main validation reference, or may be redundant and thus supplement other validation data, such as the mating geometry between the validation tracker device 90 and the altered bone. In another embodiment, with reference to FIG. 4, the robot arm 20 may be in a fixed relation to the bone during resection. In such a case, the coordinate system obtained in 101 and/or 102 may be transferred to the robot arm 20, such that the tracking of the robot arm 20 may include a tracking of surfaces and/or landmarks of the bone. This may allow a surgeon or surgical team member to switch between optimal tracking methodologies during a surgical procedure. For example, landmarks digitized and/or cut guide positioned using the tracking apparatus 70 can have their coordinates transferred to the tracking of robot arm 20. With reference to FIG. 5A, the robot arm 20 maintaining the coordinate system, the CAS system 10 can determine if the fit of the validation tracker device 90 is not as expected from the tracking of the robot arm 20.

According to 106, if a variation is present, the CAS system 10 may determine the alterations required. The determination may be in the form of remedial steps, quantitative data, etc. For example, in 106, the CAS system 10 may drive the robot arm 20 to reposition the cut guide 26, in a manner similar to that shown in FIG. 4, for another cut to be performed. The determination of alterations being required may also include the selection of a new implant. For example, if the alterations that are quantified in 105 exceed the initial implant's capacity of achieving desired parameters (e.g., varus-valgus, limb length, anteversion and inclination in the shoulder or hip), the CAS system 10 may suggest another implant, or receive the identity of another implant selection. Then, using the 3D geometry of the implant, the CAS system in 106 may calculate the additional alterations. The presence of pegs 92 may preclude the proper contact between the validation tracker device 90 and the altered bone. As described above, the validation tracker device 90 may have verification bore(s) 92 with a removable peg(s) 92. In such a case, the peg(s) 92 could be removed for the validation tracker device 90 to have its contact surface applied directly against the alterations on the bone (e.g., cut planes). The registration could then be performed for example relative to the additional landmarks, to quantity the additional alterations required.

If there are numerous alterations, such as different cut planes as in FIG. 5B, another validation tracker device 90 could be used. In the example of FIG. 5B, the other validation tracker device 90 could be applied against the planes in the anterior part of the bone, which planes are shown not contacting the tracker device 90.

In accordance with the method 100, the CAS system 10 could repeat 103, 104 and/or 105 after a determination under 106. Although the method 100 is described with reference to the robot arm 20, the positioning of the tool in 103 can be performed manually, as based on the tracking of the tool. The tool placed manually may have a reference 71 thereon. After all cuts are made, it is contemplated to position another tracker device and/or reference such as 71B in a known relation on a trial implant to perform final validation and to perform a range of motion evaluation before implanting the permanent implant. If the robot arm 20 is attached to the patient during this time and maintains the coordinate system (steps 104-106) as detailed above, the registration of the tracked trial implant can occur automatically with reference to the tracking of the robot arm 20. The CAS system 10 may include a geometric relation between the trial implant and reference 71B to perform this automatic registration. The robot arm 20 may then be unpinned or separated from the patient to allow for free flexion and extension of the knee with the tracked trial implant in place. The CAS system 10 can then record and display the range of motion and varus/valgus condition of the repaired joint, among other output. This output may be used by the surgeon can decide if any further alterations are necessary prior to implantation. The trial implant may also act as a mechanical jig to determine if the cuts are as expected.

In the embodiment of FIGS. 3A-5B, the PSI tracker device 80 and validation tracker device 90 are of limited invasiveness for the bone. The tracker devices 80 and 90 may be qualified as being pinless, as no pins (e.g., Steinmann pins) may be required to use them. The tracker device 80 may rely on its PSI surface 81 to have a robust contact with the bone, with the fastener(s) 82' inserted in a limited depth of the bone, if even used. In an embodiment, the fastener's depth is less than a depth of the cut DC, such that the fastener hole may be entirely located in bone that will be resected. The validation tracker device 90 may also be pinless, in that it may be used with temporary pegs that are located in peg holes that are present to accommodate pegs of the implant. In another embodiment, pegs are on the contact surface 91 of the validation tracker device 90.

The invention claimed is:

1. A system for validating bone alterations during computer-assisted surgery, comprising:
   a processing unit; and
   a non-transitory computer-readable memory communicatively coupled to the processing unit and comprising computer-readable program instructions executable by the processing unit for:
   registering a surface of a bone in a coordinate system using a geometry of a patient specific tracker device on the surface of the bone;
   tracking a tool relative to the bone in the coordinate system as a function of implant geometry and of a planned implant position and orientation on the bone; and
   validating at least one alteration to the bone using a mating geometry of a validation tracker device applied to an altered surface of the bone.

2. The system according to claim 1, wherein the computer-readable program instructions executable are further for determining additional alterations required after the validating.

3. The system according to claim 1, wherein the computer-readable program instructions executable are further for registering landmarks in the coordinate system related to the bone, and wherein validating the at least one alteration to the bone includes validating the at least one alteration with the registered landmarks.

4. The system according to claim 1, wherein the computer-readable program instructions executable are further for tracking the surface of the bone in the coordinate system simultaneously with the tracking of the tool.

5. The system according to claim 1, wherein the mating engagement is a patient-specific unique coupling engagement, and wherein validating the at least one alteration to the bone using a mating geometry of a validation tracker device includes using a model of the validation tracker device and the patient-specific unique coupling engagement between the validation tracker device and the bone to locate the at least one alteration relative to the bone.

6. The system according to claim 1, wherein the computer-readable program instructions executable are further for locating an axis of the bone relative to said surface.

7. The system according to claim 1, wherein the computer-readable program instructions executable are further for tracking a registration tool digitizing points on the surface of the bone.

8. The system according to claim 1, wherein tracking a tool relative to the bone includes determining a cut plane in the bone.

9. The system according to claim 1, wherein tracking a tool relative to the bone includes tracking the tool while altering the bone.

10. A system for validating bone alterations during computer-assisted surgery, comprising:
    a tracking apparatus;
    a patient-specific tracker device with a trackable reference, the patient specific tracker device having at least one contact surface being a negative of a pre-operative surface of the bone;
    a validation tracker device with a trackable reference, the patient specific tracker device having at least one contact surface for mating with an alteration on the bone;
    a processing unit; and
    a non-transitory computer-readable memory communicatively coupled to the processing unit and comprising computer-readable program instructions executable by the processing unit for:
    registering the pre-operative surface of the bone in a coordinate system using a geometry of the patient-specific tracker device and readings from the tracking apparatus;
    tracking a tool relative to the bone in the coordinate system as a function of implant geometry and of a planned implant position and orientation on the bone, using readings from the tracking apparatus; and
    validating at least one alteration to the bone using a mating geometry of the validation tracker device applied to an altered surface of the bone.

11. The system according to claim 10, wherein the computer-readable program instructions executable are further for determining additional alterations required after the validating.

12. The system according to claim 10, wherein the computer-readable program instructions executable are further for registering landmarks related to the bone, and wherein validating alterations to the bone includes validating the at least one alteration with the landmarks.

13. The system according to claim 10, wherein the computer-readable program instructions executable are further for tracking the surface of the bone with the readings from the tracking apparatus.

14. The system according to claim 10, wherein the computer-readable program instructions executable are further for tracking the surface of the bone in the coordinate system simultaneously with the tracking of the tool.

15. The system according to claim 10, wherein the validation tracker device configured for mating engagement with a patient-specific unique coupling engagement, and wherein validating the at least one alteration to the bone using a mating geometry of a validation tracker device includes using a model of the validation tracker device and the patient-specific unique coupling engagement between the validation tracker device and the bone to locate the at least one alteration relative to the bone.

16. The system according to claim 10, wherein the computer-readable program instructions executable are further for locating an axis of the bone relative to said surface.

17. The system according to claim 10, wherein the computer-readable program instructions executable are further for tracking a registration tool digitizing points on the surface of the bone.

18. The system according to claim 10, wherein tracking a tool relative to the bone includes determining a cut plane in the bone.

19. The system according to claim 10, wherein tracking a tool relative to the bone includes tracking the tool while altering the bone.

20. The system according to claim 10, wherein the tracking apparatus and the trackable reference are optical.

* * * * *